(12) United States Patent
Sun et al.

(10) Patent No.: US 6,799,969 B2
(45) Date of Patent: Oct. 5, 2004

(54) WAX-LIKE POLYMERIZABLE DENTAL MATERIAL, METHOD AND SHAPED PRODUCT

(75) Inventors: Benjamin J. Sun, York, PA (US); Andrew M. Lichkus, York, PA (US)

(73) Assignee: Dentsply Research & Development Corp.

( * ) Notice: Subject to any disclaimer, the term of this patent is extended or adjusted under 35 U.S.C. 154(b) by 109 days.

(21) Appl. No.: 10/306,096

(22) Filed: Nov. 27, 2002

(65) Prior Publication Data

US 2003/0113689 A1 Jun. 19, 2003

Related U.S. Application Data

(63) Continuation of application No. 09/670,364, filed on Sep. 26, 2000, now abandoned.
(60) Provisional application No. 60/201,705, filed on May 3, 2000, and provisional application No. 60/164,893, filed on Nov. 10, 1999.

(51) Int. Cl.$^7$ ............................................. A61D 13/00
(52) U.S. Cl. ........................... 433/167; 264/16; 523/115
(58) Field of Search ............................... 433/167, 199.1; 523/109, 113, 115, 116; 264/16, 17, 18, 19

(56) References Cited

U.S. PATENT DOCUMENTS

| | | | |
|---|---|---|---|
| 4,017,971 A | 4/1977 | Hazar | 32/2 |
| 4,094,067 A | 6/1978 | Hazar | 32/2 |
| 4,097,992 A | 7/1978 | Hazar | 32/2 |
| 4,133,110 A | 1/1979 | Bernstein et al. | 32/2 |
| 4,161,065 A | 7/1979 | Gigante | 32/2 |
| 4,175,322 A | 11/1979 | Tureaud | 433/171 |
| 4,247,287 A | 1/1981 | Gigante | 433/199 |
| 4,248,807 A | 2/1981 | Gigante | 264/18 |
| 4,259,074 A | 3/1981 | Link | 433/214 |
| 4,267,133 A * | 5/1981 | Kohmura et al. | 264/18 |
| 4,345,900 A | 8/1982 | Katz et al. | 433/171 |
| 4,375,966 A | 3/1983 | Freeman | 433/37 |
| 4,398,007 A * | 8/1983 | Kubota et al. | 526/273 |
| 4,457,818 A | 7/1984 | Denyer et al. | 204/159 |
| 4,468,202 A | 8/1984 | Cohen | 433/199 |
| 4,543,063 A | 9/1985 | Cohen | 433/175 |
| 4,551,098 A | 11/1985 | Blair | 433/171 |
| 4,609,351 A | 9/1986 | Blair | 433/55 |
| 4,705,476 A | 11/1987 | Blair | 433/171 |

(List continued on next page.)

FOREIGN PATENT DOCUMENTS

| | | |
|---|---|---|
| EP | 813 856 | 12/1997 |
| EP | 1 042 994 | 10/2000 |
| GB | 2 225 333 | 5/1990 |

*Primary Examiner*—Todd E. Manahan
(74) *Attorney, Agent, or Firm*—James B. Bieber (57) ABSTRACT

The invention provides a high strength dental polymeric material formed from wax-like polymerizable dental material. A wax-like polymerizable dental material formed by a process comprising blending polymerizable compounds which polymerize to form high strength dental polymeric material. The invention provides a process for making a denture including: positioning artificial teeth in wax-like polymerizable dental material, and shaping the polyermizable material into the form of a denture base. The process is completed without forming wax and without applying inorganic plaster to the artificial teeth.

32 Claims, 1 Drawing Sheet

U.S. PATENT DOCUMENTS

| | | | |
|---|---|---|---|
| 4,711,913 A | * 12/1987 | Tateosian et al. | 522/14 |
| 4,721,735 A | 1/1988 | Bennett et al. | 522/71 |
| 4,740,245 A | * 4/1988 | Futami et al. | 106/35 |
| 4,813,875 A | 3/1989 | Hare | 433/214 |
| 4,978,298 A | 12/1990 | Eliasz | 433/213 |
| 5,037,473 A | * 8/1991 | Antonucci et al. | 106/35 |
| 5,063,255 A | 11/1991 | Hasegawa et al. | 522/96 |
| 5,177,120 A | 1/1993 | Hare et al. | 433/37 |
| 5,213,498 A | 5/1993 | Pelerin | 433/37 |
| 5,304,063 A | 4/1994 | Ginsburg | 433/199 |
| 5,403,186 A | 4/1995 | Ginsburg | 433/199 |
| 5,431,563 A | * 7/1995 | Huybrechts | 433/48 |
| 5,591,786 A | 1/1997 | Oxman et al. | 533/109 |
| 5,635,545 A | 6/1997 | Oxman et al. | 523/115 |
| 5,711,668 A | 1/1998 | Huestis | 433/167 |
| 5,993,208 A | 11/1999 | Jonjic | 433/50 |
| 6,031,015 A | 2/2000 | Ritter et al. | 522/77 |
| 6,057,383 A | 5/2000 | Volkel et al. | 523/116 |
| 6,127,449 A | * 10/2000 | Bissinger et al. | 523/109 |
| 6,244,864 B1 | 6/2001 | Fujiwara et al. | 433/71 |

* cited by examiner

FIG 1

WAX-LIKE POLYMERIZABLE DENTAL MATERIAL, METHOD AND SHAPED PRODUCT

This application is a continuation of U.S. patent application Ser. No. 09/670,364 filed Sep. 26, 2000, now abandoned, and claims the benefit of U.S. Provisional Patent Application Ser. No. 60/201,705 filed May 3, 2000, and U.S. Provisional Patent Application Ser. No. 60/164,893 filed Nov. 10, 1999, and both are incorporated herein by reference in their entirety.

The invention relates to wax-like polymerizable materials. The invention provides wax-like polymerizable dental materials for making dentures. "Wax-like" as used herein refers to material which is flowable (fluid) above 40° C., and becomes dimensionally stable (solidifies: i.e. is nonfluid) at least at and below 23° C., in order of decreasing preference, within 5, 2, 1, 0.5 or 0.3 minutes.

A common prior art method of making dentures begins with an impression of a patient's mouth to form a plaster cast model (or record base). Dental wax is shaped into the form of a denture base on the cast and artificial teeth are positioned into the denture base shaped wax. The denture base shaped wax with the artificial teeth is then positioned in an articulator. The articulated denture base shaped wax with the artificial teeth is positioned in a flask mold. The volume of the flask is filled with hardenable investment material, such as plaster, which fixes the positioning of the teeth. After the investment material hardens, the wax is eliminated by melting, for example by heating the flask in boiling water, leaving the artificial teeth supported by the investment material and forming a denture base shaped mold cavity within the investment material. After a thorough cleansing of the mold cavity, a denture base resin material is introduced into the mold cavity. The denture base material then hardens to form a denture.

Volkel et al in U.S. Pat. No. 6,057,383 (and Canadian Patent Application 2207351), assigned to Ivoclar, disclose wax-like polymerizable material for making entire dental products. The prior art does not disclose a wax-like polymerizable material for forming dentures or other high strength products. The prior art does not disclose a process for making a denture, including positioning artificial teeth in high strength product forming wax-like polymerizable material supported by a base plate; shaping the polymerizable material to support the teeth; and polymerizing the material, whereby a denture is provided, which process does not require the use of conventional wax or positioning artificial teeth in a mold. These limitations of the prior art are overcome by the present invention.

It is an object of the invention to provide a high strength dental polymeric material formed from wax-like polymerizable dental material.

It is an object of the invention to provide a wax-like polymerizable dental material formed by a process comprising blending polymerizable compounds which polymerize to form high strength dental polymeric material.

It is an object of the invention to provide a method comprising forming high strength dental polymeric material from wax-like polymerizable dental material.

It is an object of the invention to provide a process for making a denture, comprising positioning artificial teeth in wax-like polymerizable dental material.

SUMMARY OF THE INVENTION

Wax-like polymerizable dental material of the invention is polymerizable to form high strength dental polymeric material. "High strength dental polymeric material" as used herein refers to polymeric material having a flexural modulus of at least 250,000 psi and a flexural strength of at least 5,000 psi. Wax-like polymerizable dental material of the invention is wax-like i.e. flowable above 40° C., and becomes dimensionally stable (solidifies and is nonfluid) at least at and below 23° C. While cooling from above 40° C. to 23° C. the wax-like polymerizable dental material preferably changes from being flowable to being dimensionally stable within 2 minutes. The wax-like polymerizable dental material is readily polymerized to form high strength dental polymeric material in shapes (or forms) of high strength dental polymeric products. Preferably high strength dental polymeric material has a flexural modulus of at least 300,000 psi and a flexural strength of at least 7,000 psi, and an un-notched impact strength of at least 2 foot-pounds/inch. More preferably high strength dental polymeric material in order of increasing preference has a flexural modulus of at least 350,000, 400,000, 450,000 or 500,000 psi and a flexural strength of at least 12,000, 15,000 and 16,000 psi, and an un-notched impact strength of at least 3.0, 3.5, 4.0 or 6.0 foot-pounds/inch. High strength dental polymeric material is preferably formed into dental products including full dentures, partial dentures, denture relines, night guards, crowns and bridges by polymerization of wax-like polymerizable dental material.

The invention provides a method of forming a high strength dental polymeric material, comprising polymerizing a wax-like polymerizable dental material. The invention provides a denture comprising: at least one artificial tooth and high strength dental polymeric material formed from the wax-like polymerizable dental material.

DETAILED DESCRIPTION OF THE INVENTION

Figure 1:
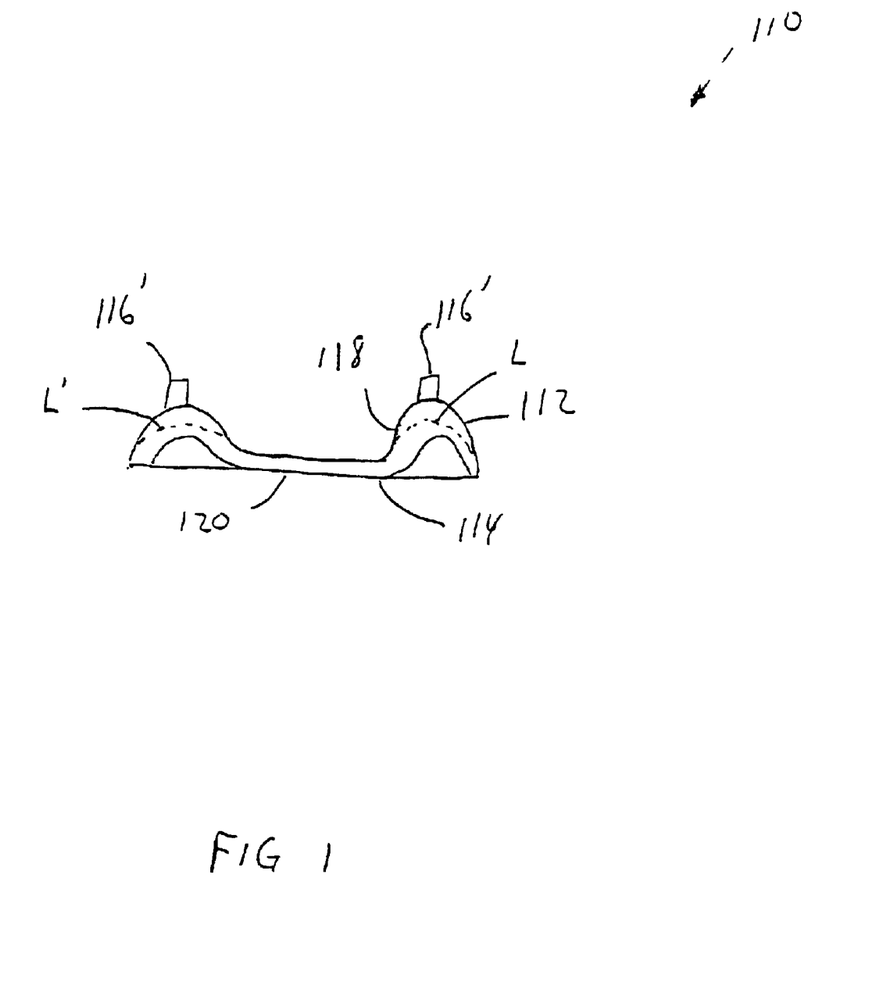
The FIGURE is a cross-sectional rear view of an uncured denture having a ridge lap and upper portion of a base plate formed from wax-like polymerizable dental material in accordance with the invention.

An embodiment of the invention is now described with more particular reference to the FIGURE. An uncured denture 110 has a ridge lap 112 and upper portion 118 of a base plate 114, are formed from wax-like polymerizable dental material. The wax-like polymerizable dental material is for example a blend of low and medium molecular weight polymerizable compounds, such as the material of Example 7. "medium molecular weight polymerizable compounds" as used herein refers to polymerizable compounds having a gram number average molecular weight between 700 and 4,000. Preferably medium molecular weight polymerizable compounds have a gram number average molecular weight between 900 and 2500. "low molecular weight polymerizable compounds" as used herein refers to polymerizable compounds having a gram number average molecular weight between 200 and 1,000. Preferably low molecular weight polymerizable compounds have a gram number average molecular weight between 350 and 800. The ridge lap 112 is positioned above dashed lines L and L' and integrally connected to lower portion 120 of the base plate 114. A lower portion 120 of the base plate 114 is made from polymeric material, which includes a medium molecular weight polymerizable compound, such as the oligomer of Example 2. Artificial teeth 116 and 116' are affixed to and supported by the ridge lap 112. The uncured denture 110 is cured as described in Example 10.

In a preferred embodiment of the invention, a wax-like polymerizable dental material is provided on a polymeric base plate made from an impression of a patient's mouth. Artificial teeth are positioned in the wax-like polymerizable dental material which is then shaped by melting and resolidifying. Then the wax-like polymerizable dental material is polymerized to form a denture. Thus the denture is formed without applying inorganic plaster to the artificial teeth and without positioning artificial teeth in a mold as required by conventional lost wax or other similar prior art methods of forming a denture.

Preformed curable dental devices and sheets for making curable dental devices may be stored at solidification temperatures at which wax-like polymerizable dental material is partially crystalline, resulting in the effective dimensional stability of the material. Preferably solidification temperatures are at or below 37° C., more preferably below 25° C. and most preferably below 20° C.

Working, such as molding, shaping, and/or carving of wax-like polymerizable dental material is carried out at flowable temperatures at and above room temperature or at solification temperatures. Working of the wax-like polymerizable dental material is preferably carried out at about 23–40° C. By heating from solidification temperatures the polymerizable material first enters its softening temperatures wherein it is partially crystalline and the presence of a flowable amorphous phase results in the some flowability of the material. "Softening temperature" as used herein refers to softening point of resins determined by the ring-and ball apparatus by ASTM method E28 (1997). Preferably, softening temperatures of the wax-like polymerizable dental material are at and above 24° C., more preferably at and above 30° C. Preferably reduced crystallinity temperatures of material are at and above 30° C., more preferably at and above 37° C. By heating from reduced crystallinity temperatures the wax-like polymerizable dental material becomes non-crystalline, resulting in effective full free flowability. Preferably non-crystalline temperatures of rapid partial crystallizable polymerizable material are at and above room temperature, for example at or above 24° C., more preferably at and above 37° C. and most preferably at and above 60° C.

Preferably wax-like polymerizable dental material of the invention after 72 hours at room temperature has a percent crystallinity of from 2 percent to 90 percent, most preferably from 5 to 75 percent. Preferably the material of the invention after 72 hours at room temperature has an enthalpy of fusion at least 2 J/g, according to ASTM testing methods E793 and D4591, more preferably at least 5 J/g, most preferably at least 10 J/g.

By heating from non-crystalline temperatures, the wax-like polymerizable dental material begins to partially polymerize and the flowability of the material is reduced. Preferably partial polymerization temperatures of the material are at and above 120° C., more preferably at and above 150° C.

The dental material of the invention provides a unique combination of free flowability and dimensional stability depending on its temperature with a rapid transition between the two. In a preferred embodiment of the invention, the wax-like polymerizable dental material is provided in small volumes at flowable temperatures locally on the dental device being worked. At flowable temperatures wax-like polymerizable dental material may be continuously provided by dispensing from a heated syringe-type dispensing device, disposal dropper or mechanical or electrical dispenser.

In a preferred embodiment the wax-like polymerizable dental material of the invention is formulated as a blend of low molecular weight polymerizable compounds (200 to 1000, preferably 350–800 molecular weight range) having 20 or more percent crystallinity; and medium molecular weight polymerizable compounds (700–4000, preferably 900–2500 molecular weight range) having up to 10 percent crystallinity. The medium molecular weight compounds preferably make up 10–95 weight percent of the material and the low molecular weight compounds make up 5–90 percent by weight of the unfilled material.

Wax-like polymerizable dental material of an embodiment of the invention, upon polymerization, provides an unpigmented solid translucent polymeric product. The material becomes transparent during polymerization as the crystallized phase melts and is polymerized. Initial polymerization of amorphous phase results in a frozen state, which prevents distortion of the product as the crystallized phase melts by the heat, generated in the polymerization and polymerizes under light irradiation.

Prior to polymerization, wax-like polymerizable dental material may be worked by heating, for example between 35–100° C., to reduce the viscosity to between 10,000 and 1 CP. At 35–100° C., the low viscosity work time is between 0.05 and 12,000 minutes; more preferably, 0.2–50 minutes; and most preferably 0.5–20 minutes.

A preferred wax-like polymerizable dental material of the invention is a light curing resin, by, for example, visible or UV light. The material preferably includes initiators, inhibitors and activators (and fillers) as a single component that is essentially free of air, and packaged in material, which is opaque to activating light. The material preferably is applied by hand or instruments and is cured in a short time (about 10 seconds to about 60 minutes) by the application of activating light.

A method of the invention uses wax-like polymerizable dental material in a viscosity range from a rigid, waxy or glassy state to very soft and flexible at room temperature. Preferably, the wax-like polymerizable dental material includes: at least one compound selected from monomers, oligomers or prepolymers of this invention; polymerization initiating mixture. Optionally, filler, such as inorganic filler, is included in the wax-like polymerizable dental material.

The solid material of this invention has less shrinkage and less exotherm while polymerizing, compared to conventional powder/liquid types of polymerization or viscous liquid/powder based resins. The melting of crystallized phase of material of the invention results in volume expansion, which compensates for part of shrinkage due to polymerization. Wax-like polymerizable dental material of the invention polymerizes to form unfilled dental compositions with less than 5 weight percent shrinkage; preferably less than 4 weight percent shrinkage; more preferably, less than 3 weight percent shrinkage; most preferably, less than 2 percent shrinkage. Dentures made with wax-like polymerizable dental material of the invention are better fitting in the patient's mouth.

For direct and indirect methods of denture fabrication, the wax-like polymerizable dental material of the invention is heated to its molten or softened temperature. Preferably, it is heated in a constant temperature oven, with an electric spatula, a wax pot, a warm water bath or a heat-gun to a softened or melted state. Preferably, shaped dental products are formed from the wax-like polymerizable dental material without the use of a mold. Alternatively, low cost molds that do not need to withstand heat or more than moderate pressure are used.

The wax-like polymerizable dental materials of the invention are useful in flaskless fabrication of dentures and other dental prosthetic devices. The denture fabricator sets up teeth without the need for investment and flasking. The relative positions of teeth may be adjusted in a "try in" with the patient prior to polymerization. The denture made can then be cured in situ during the "try in" or cured in an outside light unit to an esthetic denture with superior physical and mechanical properties without any significant distortion.

Use of the wax-like polymerizable dental material in denture making beneficially reduces the time, equipment and material conventionally needed. In a preferred embodiment of the invention, the initial steps used in the prior art for making a denture, including making an impression of a patient's mouth are maintained. However, no wax model or associated flask mold is needed to make a denture when using improved dental material, methods and products of the invention. The prior function of wax and flasking are eliminated, without substituting other equipment or material for their functions in accordance with a preferred embodiment of the invention.

A wax-like polymerizable dental material of a preferred embodiment of the invention can be heated to a softened (or melted) temperature and manually shaped in the mouth, in a mold or on a cast so that it can conform to the shape of hard and soft oral tissue, a mold or a cast. A wax-like polymerizable dental material of the invention can be dimensionally controlled by cooling it down to form a shape stable form within a period of a minute to a few days. It is beneficial that the composition can be softened at a temperature above oral temperature and take on a rigid shape rapidly at oral temperature (or below) and conformed to an oral cavity, mold or cast. At an elevated temperature, above oral temperature, the composition of the invention has reasonable or desirable mass flow under the pressure of either hands, fingers or tools where imparting the shape of the material takes place. A wax-like polymerizable dental material of the invention provides sufficient strength and stiffness to allow an acceptably accurate dental impression to be made and minimal apparent mass flow of the composition under moderate pressure at temperatures below oral temperature.

A specific wax-like polymerizable dental material is a shape stable solid at 37° C. or below; a soft solid that is flowable at 40° C. or above, under limited finger pressure but not tacky; extremely soft at 60° C. and above and a liquid at 70° C. or above. Thus, the material has no mass flow at 37° C. or below, some mass flow at 40° C. or above, significant mass flow at 60° C. or above and extensive mass flow as a liquid at 70° C. or above.

A preferred wax-like polymerizable dental material of this invention has wide utility for the fabrication of provisional prosthetic devices, such as temporary crowns and bridges. The provisional prosthesis is used to protect the tooth and gingival tissues and to stabilize mobile teeth while providing comfort, function and esthetics to the patient. The provisional prosthesis is used as a temporary restoration typically for a few weeks, until the final prosthesis is cemented in place in the mouth.

Advantages of a preferred wax-like polymerizable dental material of the invention over currently used provisional prosthetic materials and crown liner materials include ease of use and cure on demand to a final set stage. Compared with currently available materials for making dentures, the wax-like polymerizable dental material of the invention has superior mechanical properties and much more desirable physical and handling properties.

Wax-like polymerizable dental material preferably provides dental products having high strength dental polymeric materials having unnotched impact strength, in order of increasing preference of at least: 2.0 ft-lb/in; 3.0 ft-lbs/in; 4.0 ft-lbs/in; 5 ft-lbs/in; 6.0 ft-lb/in; and 8.0 ft-lbs/in; notched impact strength, in order of increasing preference is at least: 0.7 ft-lbs/in; 0.85 ft-lbs/in; 0.9 ft-lbs/in; 1.0 ft-lbs/in; 1.1 ft-lbs/in; 1.2 ft-lbs/in; and flexural strengths, in order of increasing preference, at least: 5000 psi; 7000 psi; 10,000 psi; 12000 psi. "Flexural strength, and flexural modulus" as used herein refers to results of testing according to ASTM D790 (1997). "Notched impact strength" and "un-notched impact strength" as used herein are measured by ASTM D256 (1997).

Preferably, polymerizable compounds used in wax-like polymerizable dental material are formed by known methods of partial crystallization. Polymerizable compounds which are readily partially crystallizable preferably have in order of increasing preference from 0.1 to 10 percent, from 0.5 to 10 percent, from 1 to 8 percent groups which act as nucleation sites. Urethane compounds, which are readily partially crystallizable, may be partially crystallized for example by providing water to excess NCO groups in a molar ratio of from 0.3 to 3 and from 3 to 0.3. Wax-like polymerizable dental material of the invention has in order of increasing preference from 2 to 80 percent crystallinity by weight at 37° C., from 2 to 60 percent crystallinity by weight at 37° C., from 5 to 70 percent crystallinity by weight at 37° C., from 10 to 50 percent crystallinity by weight at 37° C.

Compounds which are readily partially crystallizable and useful in wax-like polymerizable dental material of a preferred embodiment of the invention include methacrylate (or acrylate) compounds prepared for example by reaction of a urethane pre-oligomer with hydroxylalkymethacrylate. Preferably such compounds have a structure within the scope of one of general formulas I–V below. Preferably the urethane pre-oligomer is linear, comprises isocyanate end groups and has a structure within the scope of general formula I:

wherein $R_1$ and $R_2$ are either an alkyl having from 1 to 14 carbon atoms or containing at least an aromatic group having from 6 to 14 carbon atoms, m is an integer from 0 to 20, the value of m in the oligomer depends on the molar ratio of diisocyanate to diol used, and the value of m increases as this molar ratio decreases. The diisocyanate portion has the structure OCN—$R_1$—NCO and the diol portion has the structure HO—$R_2$—OH.

Alternatively, urethane pre-oligomer is formed by reaction of at least one diol with excess, at least one diisocyanate to yield a urethane pre-oligomer having a structure within the scope of one or more of general formulas: II–IV wherein $R_1$, $R'_1$, $R_2$ and $R'_2$ each independantly is an alkyl having from 1 to 14 carbon atoms or at least an aromatic group having from 6 to 14 carbon atoms, n and m are each independently integers from 0 to 20, the sum of n and m is at least 1, the value of n in the oligomer depends on the molar ratio of diisocyanates to diols used, and the value of the sum of n and m increases as this molar ratio decreases. The diisocyanates have the structures OCN—R$_1$—NCO and OCN—R'$_1$—NCO and the diols have the structures HO—R$_2$—OH and HO—R'$_2$—OH. The more complex structures of urethane pre-oligomer are constructed from at least two different diols and at least two different diisocyanates.

Reaction of the urethane pre-oligomer with the ethylenically unsaturated monomer as defined below yields a polymerizable compound having the structure within the scope of the general formula V:

$$CH_2=C(R_3)-CO_2-R_4-CO-NH-(R_1-NH-CO-O-R_2-O-OC-NH)n-R_1-NH-CO-R_4-O_2C-C(R_3)=CH_2 \quad \text{v}$$

wherein R$_3$ is hydrogen, or an alkyl, such as a methyl group, and R$_4$ is an alkyl group having from 1 to 14 carbon atoms, and n is an integer from 0 to 20. The typical ethylenically unsaturated monomer is a hydroxyalkyl(meth)acrylate, e.g. 2-hydroxyethyl methacrylate, hydroxypropyl methacrylate, caprolactone 2-(methacryloyloxy)ethyl ester, etc.

Preferred mechanical properties of cured resin and the adequate handling properties of compositions, polymerizable compound, are present when the value of n in the compound is not greater than 10; more preferably n is not greater than 5. The preferred value of n in the compound largely depends on the requirements of the specific application. The most preferable value of n in the compound for aromatic ring based diol is between 1 and 3. Therefore, the molar ratio of diisocyanate to diol for aromatic ring based diol is most preferable between 1.33 and 2. The most preferable value of n in the compound for alkyl based diol is between 1 and 4. Therefore, the molar ratio of diisocyanate to diol for alkyl based diol is most preferable between 1.25 and 2.

Catalysts known in the art may be used to accelerate the formation of the isocyanate-ended pre-oligomer and end-capped ethylenically unsaturated monomer, for examples, tertiary amines and metal salts, e.g. stannous octoate and in particular dibutyl tin dilaurate.

Preferably compounds of the invention have at least one ethylenically unsaturated double bond and are either a microcrystalline solid (paste, soft, rigid or glassy solid) or amorphous solid (paste, soft or glassy solid) at room temperature. Preferably compounds of the invention are difunctional methacrylates including reaction products of bisphenol A propoxylate, 1,6-diisocyanatohexane and 2-hydroxyethyl methacrylate, reaction products of bisphenol A propoxylate, trimethyl-1,6-diisocyanatohexane and 2-hydroxyethyl methacrylate, a series of reaction products of bisphenol A, trimethyl-1,6-diisocyanatohexane and 2-hydroxylethyl methacrylate, a series of reaction products of bisphenol A, 1,6-diisocyanatohexane and 2-hydroxylethyl methacrylate, a series of reaction products of trimethyl-1,6-diisocyanatohexane, 2,5-dimethyl-2,5-hexanediol and 2-hydroxyethyl methacrylate, a series of reaction products of trimethyl-1,6-diisocyanatohexane, 1,6-diisocyanatohexane, 2,5-dimethyl-2,5-hexanediol and 2-hydroxyethyl methacrylate, a series of reaction products of trimethyl-1,6-diisocyanatohexane, 1,6-diisocyanatohexane, bisphenol A propoxylate and 2-hydroxyethyl methacrylate, caprolactone 2-(methacryloyloxy)ethyl ester, and derivatives of above compounds, etc.

Diisocyanates useful for making wax-like polymerizable dental material of the invention include trimethyl-1,6-diisocyanatohexane, 1,6-diisocyanatohexane, 1,8-diisocyanatooctane, isophorone diisocyanate, 4,4'-methylenebis(cyclohexyl isocyanate), cyclohexyl diisocyanate, 3-methylhexane-1,6-diisocyanate, 3-ethyl-1,6-hexanediisocyanate, 5-methyl-1,9-nonanediisocyanate, 5-ethyl-1,10-decanediisocyanate, 2,3-dimethyl-1,6-hexanediisocyanate, 2,4-dimethyl-1,8-octanediisocyanate, 2,4,6-trimethyl-1,7-heptanediisocyanate, 2,3-dimethyl-5-ethyl-1,8-octanediisocyanate, 2-methyl-4,6,8,10-tetrapropyl-1,12-dodecanediisocyanate and the like, and mixtures thereof. Examples of diisocyanates that are also suitable include aromatic diisocyanates, for example, 4,4-methylene bis(phenyl isocyanate), 2,4-tolylene diisocyanate, 2,6-tolylene diisocyanate, 1,4-phenyl diisocyanate, 1,5-naphthalene diisocyanate, 1,3-bis (isocyanatomethyl)benzene, 1,3-bis(isocyanato-1-methylethyl)benzene, 1,3-bis(isocyanatomethyl) cyclohexane, 3,3'-bitoluene diisocyanate, 1,4-xylylene diisocyanate and the like, and mixtures thereof. Any of known organic diisocyanates and their mixtures may be used in this invention. Other diisocyantes can be readily prepared by employing well-known procedures, such as phosgenation of the diamine hydrochloride.

Examples of suitable diols include 1,4-butanediol, 1,6-hexanediol, 1,10-decanediol, 1,9-decanediol, 1,12-dodecanediol, 1,14-tetradecanediol, 2,5-dimethyl-2,5-hexanediol, hydrogenated bisphenol A, bisphenol A, propoxylated bisphenol A, ethoxylated bisphenol A, bis(2-hydroxyethyl) terepthalate, and mixtures thereof. Any of known organic diol compounds having hydroxyl functionality any be used.

Examples of suitable methacrylates or acrylates include 2-hydroxyethyl methacrylate, 2-hydroxyethyl acrylate, 2-hydroxypropyl methacrylate, 3-hydroxypropyl methacrylate, hydroxypropyl acrylate, glycerol dimethacrylate, glycerolmonomethacrylate, 2-hydroxyethyl acrylate, hydroxypropyl acrylate, 4-hydroxybutyl methacrylate, 4-hydroxybutyl acrylate, 2-hydroxy-3-phenoxypropyl acrylate, 2-hydroxycyclohexyl methacrylate, caprolactone 2-(methacryloyloxy)ethyl ester, pentaerythritol triacrylate, 2-hydroxycyclohexyl acrylate, and the like, and mixture thereof. Any of known hydroxyalkyl (meth)acrylate may be used in this invention.

Wax-like polymerizable dental material may include one or more initiating systems to cause them to harden promptly. Light curable wax-like polymerizable dental materials preferably include a light sensitizer, for example camphorquinone, Lucirin TPO, or methyl benzoin which causes polymerization to be initiated upon exposure to activating wavelengths of light; and/or a reducing compound, for example tertiary amine.

A room temperature or heat activating catalyst system is preferably included in the wax-like polymerizable dental material of the invention. Preferably included is a peroxide capable of producing free radicals when activated by a reducing agent at room temperature or heat at an elevated temperature. Preferred peroxides include benzyl peroxide and lauroyl peroxide. Suitable promoters include the same reducing agents and accelerators used in well-known initiating systems.

A method of the invention beneficially provides a patient with a denture in a single office visit. This process for making a denture, includes: forming a denture on a stone model of the patient dentition of wax-like polymerizable dental material of the invention and artificial teeth; positioning in the patient's mouth the denture of polymerizable material supporting the artificial teeth; and, polymerizing the polymerizable material to finally form the denture. In a preferred embodiment of the invention the process includes shaping the polymerizable material to the patient's mouth.

A preferred embodiment of the invention provides a process for making a denture, including: positioning artificial teeth in wax-like polymerizable dental material, and shaping the polymerizable material into the form of a denture base. The process is completed without forming a coventional lost wax mold or applying inorganic plaster to the artificial teeth.

Wax-like polymerizable dental materials of the invention are believed to rapidly partially recrystallize. This rapid recrystallizability provides a unique combination of free flowability and dimensional stability, depending on its temperature. The material rapidly transitions from a freely flowable state by means of rapid crystallization to a dimensionally stable state. The material at solidification temperatures is partially crystalline and the crystallinity present in an amorphous phase results in the effective dimensional stability of the material. The material at flowable temperatures is non-crystalline and the absence of crystallinity results in the effective free flowability of the material. "Crystallinity" as used herein refers to regularity and order within a material resulting in a heat of fusion of at least 1.0 J/g at and below 50° C. "Heat of Fusion" as used herein refers to enthalpy of fusion as determined by ASTM 793-95. Percent crystallinity is determined by measuring the heat of fusion using differential scanning calorimetry according to ASTM test method E 793-95.

The wax-like polymerizable dental material of the invention is useful for formation of dental products including full dentures, partial dentures, denture liners, custom trays, artificial teeth, repairs for natural teeth, veneers, denture repairs, denture reline, night guards, splints, retainers, orthodontic components, crowns, bridges, provisional dental devices, inlays, onlays, and tooth restorative fillings, orthodontic appliances, oral orthopedic appliances, temporary/provisional dentures or partial dentures; maxillofacial prostheses, obturators, and occular prostheses.

Compositions in accordance with the invention may further include fillers, pigments, stabilizers, plasticizers and fibers. Preferably, polymerizable dental compositions in accordance with the invention include from about 2 to about 95 percent by weight filler particles. More preferably, these compositions include from about 10 to about 85 percent by weight filler. Nanocomposites and ceramers may be formed from these composites. The fillers preferably include both organic and inorganic particulate fillers to further reduce polymerization shrinkage, improve wear resistance and modify the mechanical and physical properties. Fillers useful in the compositions of the invention include organic fillers, such as particulate polymer, and inorganic filler, such as fumed silica, ground silica, glass, ceramic, and glass ceramic. Preferred polymers useful as fillers in the compositions of the invention include butadiene styrene polymers and methacrylated butadiene styrene polymers. Polymerizable compositions in accordance with a preferred embodiment of the invention include from 2 to 90 percent by weight of polymer particles including rubber particles. More preferably, these polymerizable compositions include from 5 to 70 percent by weight of polymer particles including rubber particles. Most preferably, these polymerizable compositions include from 10 to 50 percent by weight of polymer particles including rubber.

A preferred embodiment of the invention provides a method of restoring a natural dental tooth, comprising: applying polymerizable material to the natural dental tooth, a portion of the polymerizable material being dimensionally stable and a portion of the polymerizable material being flowable, and light curing the polymerizable material to form a restored natural dental tooth.

Preferred stabilizers used in this invention are butylated hydroxytoluene (BHT) and the methyl ether of hydroquinone (MEHQ).

A preferred embodiment of the invention provides a denture comprising a tooth and denture base, wherein the tooth comprises an interpenetrating polymer network polymeric matrix and at least 0.1 percent by weight of self-lubricating particles having a particle size less than 500 microns effectively bonded to and distributed in the polymeric matrix. The denture has a bond strength between the tooth and the denture base of at least 4,480 psi.

A perferred embodiment of the invention provides a high strength dental polymeric material formed from wax-like polymerizable dental material. Preferably the wax-like polymerizable dental material is shaped into at least a portion of a denture base and the high strength dental polymeric material is formed by light curing and has an un-notched impact strength of at least 2 foot-pound/inch. Preferably the wax-like polymerizable dental material is shaped into at least a portion of a denture base and the polymeric material has flexural modulus of at least 400,000 psi and a flexural strength of at least 7,000 psi and an un-notched impact strength of at least 2 foot-pounds/inch.

A perferred embodiment of the invention provides a wax-like polymerizable dental material formed by a process comprising blending polymerizable compounds which polymerize to form high strength dental polymeric material. Preferably the wax-like polymerizable dental material is shaped into at least a portion of a denture base and the polymeric material has flexural modulus of at least 350,000 psi and a flexural strength of at least 7,000 psi and an un-notched impact strength of at least 2 foot-pounds/inch. Preferably the high strength dental polymeric material has a flexural modulus of at least 400,000 psi and a flexural strength of at least 12,000 psi and an un-notched impact strength of at least 4 foot-pounds/inch.

A perferred embodiment of the invention provides a method comprising forming high strength dental polymeric material from wax-like polymerizable dental material. Preferably the high strength dental polymeric material is at least a portion of a denture. Preferably the denture is formed without shaping wax. Preferably the wax-like polymerizable dental material is shaped into at least a portion of a denture base and polymerized to form polymeric material having an un-notched impact strength of at least 2 foot-pound/inch. Preferably the polymeric material has an un-notched impact strength of at least 5 foot-pound/inch. Preferably the polymerizable material is flowable at and above 40° C., dimensionally stable at and below 25° C., and adapted to form polymeric material having a flexural modulus of at least 300,000 psi, and flexural strength of at least 7,000 psi. Preferably the method includes providing shaping the wax-like polymerizable dental material into a form of at least a portion of a dental device, and curing the wax-like polymerizable dental material to form high strength dental polymeric material having the shape. Preferably the polymerizable material is heated between 40° C. and 180° C. Preferably the polymerizable material is flowable at and above 40° C. and further comprising positioning at least one artificial tooth in the polymerizable material. Preferably the method includes positioning polymerizable material over the artificial tooth. Preferably the polymerizable material is adapted to become dimensionally stable within 90 minutes. Preferably the polymerizable material is adapted to become dimensionally stable within 5 minutes. Preferably the dental device is a full denture, partial denture, denture liner, custom tray, artificial tooth, veneer, night guard, splint, retainer, orthodontic component, crown, bridge, dental device, restorative fillings, inlay or onlay. Preferably the method includes supporting a U-shaped preformed set of artificial teeth on the polymerizable material. Preferably the method includes providing additional polymerizable material, a major portion of the additional polymerizable material being dimensionally stable and a minor portion of the additional polymerizable material being flowable, light curing the additional polymerizable material to form a repaired dental device.

A perferred embodiment of the invention provides a process for making a denture, comprising positioning artificial teeth in wax-like polymerizable dental material. Preferably the wax-like polymerizable dental material is supported by a base plate, and further comprising shaping the wax-like polymerizable dental material.

A perferred embodiment of the invention provides a method for making a dental product comprising mounting artificial teeth in wax-like polymerizable dental material. Preferably the wax-like polymerizable dental material is supported by a composition which is not wax-like. Preferably the method includes polymerizing the wax-like polymerizable dental material to form a portion of the dental product. Preferably the method includes melting and resolidifing the wax-like polymerizable dental material.

A perferred embodiment of the invention provides a denture comprising: at least one artificial tooth and high strength dental polymeric material formed from wax-like polymerizable dental material. Preferably the wax-like polymerizable dental material is shaped into at least a portion of a denture base and polymerized to form high strength dental polymeric material having an un-notched impact strength of at least 2 foot-pound/inch. Preferably the wax-like polymerizable dental material is shaped into at least a portion of a denture base and polymerized to form high strength dental polymeric material.

A perferred embodiment of the invention provides a method, comprising: polymerizing a wax-like polymerizable dental material to form a high strength dental polymeric material. Preferably the high strength dental polymeric material is at least a portion of a full denture, partial denture, night guard or bridge. Preferably the wax-like polymerizable dental material is shaped into at least a portion of a denture base and the polymeric material has an un-notched impact strength of at least 2 foot-pound/inch. Preferably the wax-like polymerizable dental material is shaped into at least a portion of a denture base. Preferably the method includes light curing the wax-like polymerizable dental material. Preferably the method includes shaping wax-like polymerizable dental material to form a dental product. Preferably the wax-like polymerizable dental material is shaped into at least a portion of a denture base and the high strength dental polymeric material has flexural modulus of at least 300,000 psi and a flexural strength of at least 7,000 psi and an un-notched impact strength of at least 4 foot-pounds/inch.

The following examples are offered to aid in understanding the invention and are not to be construed as limiting its scope. Unless otherwise indicated, all parts and percentages are by weight; Lucirin TPO refers to 2,4,6-trimethylbenzoyldiphenylphosphine oxide made by BASF. The visible light curing unit used in the following examples was a TRIAD VLC visible light curing unit modified by adding a fifth light to provide 30 milliwatts/cm$^2$ of from 350 to 450 nm light.

EXAMPLE 1

Prepartion of Oligomer

A three-neck flask was charged with trimethyl 1,6-diisocyanatohexane (36.3 g, 0.173 mol) under dry nitrogen flow. The flask was placed in an oil bath with an overhead stirrer and the oil bath was heated to about 31° C. under a positive nitrogen pressure. Comonomer 1,10-decanediol (20.9 g, 0.120 mol) was charged into this reactor under constant stirring and followed by the addition of catalyst dibutyltin dilaurate (0.1 g, 2×10$^{-4}$ mol). The temperature of the oil bath was maintained between 51 and 75° C. for four hours. To this clear viscous isocyanate end-capped product, 16.5 g (0.127 mol) of 2-hydroxyethyl methacrylate was added. The temperature of oil bath was controlled between 50 to 60° C. Six hours later, the heat was turned off, the flask was removed and oligomer was collected and stored in a dry atmosphere.

EXAMPLE 2

Preparation of Oligomer

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

EXAMPLE 3

Preparation of Monomer

A reaction flask was charged with 700 grams of 1,6-diisocyanatohexane and heated to about 70° C. under a positive nitrogen pressure. To this reactor, 1027 grams of 2-hydroxyethyl methacrylate, 0.75 gram of catalyst dibutyltin dilaurate and 4.5 grams of butylated hydroxy toluene (BHT) were added slowly under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

EXAMPLE 4

Preparation of Polymerizable Denture Contour Material

A wax-like polymerizable dental material was prepared by stirring at 85° C. a liquid mixture of 63.0 grams of oligomer made the procedure of Example 2 and 37.0 grams of compound of Example 3. To this mixture, 1.5 grams of initiating mixture (23.02% of MMA (Methacrylic acid); 1.3% BHT (Butylated hydroxy toluene); 46.05% DMADPA (N, N-Dimethylaminoethyl-neopentyl acrylate); 16.32% Silane (Gammamethacryloxy-propyltrimethoxysilane); and 13.31% CQ (camphorquinone), 0.1 gram of red acetate fibers and 0.31 gram of pigment concentrates were added.

EXAMPLE 5

Preparation of Polymerizable Denture Base Plate Material

A light curable polymerizable material was prepared by stirring at 85° C. a liquid of 64.1 grams (99.5% by weight) of oligomer of Example 2, 0.224 gram (0.35% by weight) of 2,4,6-trimethylbenzoyldiphenylphosphine oxide, (Lucirin TPO made by BASF), 0.064 gram (0.1% by weight) of red acetate fibers and 0.192 gram of pigment concentrates (0.05% by weight of pigment).

EXAMPLE 6

Preparation of Polymerizable Denture Base Plate (or Reline) Material

A light curable polymerizable material was prepared by stirring at 85° C. a liquid of 98.0 grams of TBDMA oligomer of Example 2, 0.35 gram of 2,4,6-trimethylbenzoyldiphenylphosphine oxide, (Lucirin TPO made by BASF), 1.5 gram of solution containing 8.3% camphorquinone (CQ), 25% ethyl 4-dimethylaminobenzoate (EDAB) and 66.7% 1,6-hexanediol dimethacrylate (HDDMA), 0.1 gram of red acetate fibers and 0.05 gram of pigment.

EXAMPLE 7

Preparation of Polymerizable Wax-like Denture Contour Material

A light curable wax-like polymerizable dental material was prepared by stirring at 85° C. a liquid mixture of 50.5 grams of oligomer of Example 2, 45.0 grams of monomer of Example 3 and 4.0 grams of stearyl acrylate from Sartomer. To this mixture, 0.35 gram of 2,4,6-trimethylbenzoyldiphenylphosphine oxide (Lucirin TPO), 0.1 gram of red acetate fibers and 0.05 gram of pigment concentrates were added. The polymerizable wax-like material formed becomes flowable at 65 to 68° C.

EXAMPLE 8

Preparation of Polymerizable Denture Set-up Material

A light curable polymerizable material was prepared by stirring at 85° C. a liquid mixture of 84.5 grams of oligomer of Example 2 and 15.0 grams of monomer of Example 3. To this mixture, 0.35 gram of 2,4,6-trimethylbenzoyldiphenylphosphine oxide (Lucirin TPO), 0.1 gram of red acetate fibers and 0.05 gram of pigment were added.

EXAMPLE 9

Preparation of a Denture without Forming a Mold Cavity of a Denture Base

A plaster cast of a patient's mouth is coated with a release agent and 70 grams of the product composition of Example 4 and warmed to 51° C. in an oven. The composition is applied and shaped using finger pressure and trimming to form a baseplate which hardens when cooling to room temperature. A quantity of the composition of Example 4 is formed into a rope and applied to the baseplate of the type shown in the FIGURE at 114. Artificial teeth are pressed into the rope, which is adapted to adequately cover the appropriate surfaces of the teeth to provide support for the teeth. Additional amounts of composition of Example 4 are applied between the teeth and the baseplate to fully embed the teeth. Hot air from a small nozzle hot air gun is applied to melt the composition of Example 4 and let it flow into fissures between teeth and to smooth the outer surface of the denture. This forms a ridge lap 112 as shown in the FIGURE. The lingual and buccal surfaces of the denture are contoured, trimmed and carved using an electronic hot spatula and hot air gun. The denture is placed in the patient's mouth for try-in at a dental office and tooth positions are adjusted. The denture is fitted to the cast and a TRAID Air Barrier Coating is painted on the denture and cured for 10 minutes. The cast is removed from the denture and the tissue side of the denture is painted with TRIAD Air Barrier Coating and cured in the visible light curing unit for 4 minutes. When cured, the denture is washed with water to remove all traces of Air Barrier Coating. The denture is then finished and polished.

EXAMPLE 10

Preparation of a Denture without Forming a Mold Cavity of a Denture Base

A plaster cast of a patient's mouth is coated with a release agent (e.g., Al-Cote and Isolant sold by Dentsply International Inc. or Teflon solution such as Krytox from Dupont) and heated to 55° C. in an incubator. An arch-shaped baseplate resin containing 14 grams of the product composition of Example 6 is applied and shaped onto the warm cast. The resin is shaped and flowed to fully cover the cast, using finger pressure and trimming to form a baseplate. The baseplate is cured for 10 minutes in the visible light curing unit.

A sufficient quantity of the composition of Example 8 is formed into a rope. The rope is applied to the baseplate. Then artificial teeth are pressed into the rope with the thickness of the rope adapted to adequately cover the appropriate surfaces of the teeth to provide support. Melted composition of Example 7 from an about 87° C. wax pot is applied by using an electric spatula between the teeth and the baseplate to fully embed teeth and to flow into fissures between teeth and to smooth the outer surface of the denture. Hot air from a small nozzle hot air gun may also be applied to let composition of Example 7 flow into fissures between teeth and smooth the outer surface of the denture. The lingual and buccal surfaces of the denture are contoured, trimmed and carved using a spatula. The denture is placed in a patient's mouth for try-in at a dental office and tooth positions are adjusted. The denture back is fitted to the cast and the TRIAD Air Barrier Coating is painted on the denture. Then a model release agent (MRA) sold by Dentsply International Inc. is applied to around posterior teeth and supporting resin. A strip of Triad gel is applied on surface between teeth and supporting resin to form a continuous circle and cured in a visible light curing unit for 10 minutes, followed by post curing for 8 hours of gradually cooling to 23° C. When cured, the denture is washed with water to remove all traces of Air Barrier Coating. The denture is then finished and polished.

EXAMPLE 11

Preparation of a Partial Denture without Forming a Mold Cavity (Investment) of a Denture Base A removable partial denture framework is fabricated. A separating medium is applied to a gypsum cast of the patient's dentition. A sufficient quantity of the composition of Example 6 is applied onto the edentulous areas of the cast and adapted with finger pressure or appropriate instruments. Excess material is trimmed with a hot spatula. A sufficient quantity of the composition of Example 6 is adapted into the tissue side finish line of the partial denture framework. The framework is seated on the cast firmly, embedding the uncured material of Example 6. All rests and tissue stops are varnished as correctly positioned on the cast, indicating that the framework is fully seated. Excess material is removed and these "baseplate" areas are cured in the visible light curing unit. A rope of the composition of Example 8 is adapted onto the precured baseplate/edentulous areas. The rope has a thickness sufficient to cover the ridge lap surfaces of the teeth to provide support for the teeth and to seat the teeth, which are then set up in the rope. A portion the composition of Example 7 is applied between the teeth and the baseplate. A small nozzle hot air gun is used to melt the composition of Example 7 so that it flows into the fissures between teeth as the outer surface smoothes.

The lingual and buccal surfaces of the edentulous areas are contoured, trimmed and carved using an electric hot spatula, sharp tools and hot air gun. The partial denture "wax-up" is removed from the cast for try-in. This may damage or destroy the cast. The denture is placed in a patient's mouth for try-in at a dental office and tooth positions adjusted if needed. The partial denture is fitted to a modified cast (reduced soft tissue heights of contour). TRAID Air Barrier Coating is painted onto the denture. Then a mold release agent (MRA) sold by Dentsply International, Inc. is applied around the postierior teeth and supporting resin. A strip of triad gel is applied between teeth and on the surface of the supporting resin to form a continuous circle. The denture is then cured in the visible light curing unit for 10 minutes. When cured, the partial denture is washed with water to remove all traces of Air Barrier Coating. The partial denture is then finished and polished.

TABLE

COMPARISON OF POLYMERIZABLE WAX-LIKE MATERIALS

|  | Flexural strength (psi) | Flexural Modulus (kpsi) | Un-notched Impact Strength (ft-lb/in) | notched Impact Strength (ft-lb/in) |
|---|---|---|---|---|
| U.S. Pat. No. 6,057,383 (Ivoclar) Example 7B | 2897 | 207.9 | 1.03 | 0.53 |
| Example 7 of the present invention | 16820 | 446.5 | 8.9 | 1.28 |

Example 7B of U.S. Pat. No. 6,057,383 (and Canadian Patent Application 2207351) was followed and the product thereof tested to provide the information in the above Table. The Polymerizable wax-like material of the invention made by following the procedure of Example 7 of the present invention. Comparing the test results, Example 7's flexural strength is more than 500 percent greater than that of the tested material of U.S. Pat. No. 6,057,383. Example 7 of the present invention has a flexural modulus which is more than two times greater than that of the polymerizable wax-like material of U.S. Pat. No. 6,057,383. Example 7 of the present invention has an un-notched Impact Strength which is more than eight times greater than that of the polymerizable wax-like material of U.S. Pat. No. 6,057,383. Example 7 of the present invention has a notched Impact Strength which is more than two times greater than that of the polymerizable wax-like material of U.S. Pat. No. 6,057,383. Overall results show that the material of the invention is suitable for making a denture while the flexural strength and un-notched impact strength of the comparative examples are insufficient.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A wax-like polymerizable dental material formed by a process comprising blending polymerizable compounds which polymerize to form high strength dental polymeric material.

2. The material of claim 1 wherein said wax-like polymerizable dental material is shaped into at least a portion of a denture base and said polymeric material has flexural modulus of at least 350,000 psi and a flexural strength of at least 7,000 psi and an un-notched impact strength of at least 2 foot-pounds/inch.

3. The material of claim 1 wherein said high strength dental polymeric material has a flexural modulus of at least 400,000 psi and a flexural strength of at least 12,000 psi and an un-notched impact strength of at least 4 foot-pounds/inch.

4. A method comprising
providing wax-like polymerizable dental material, and
forming high strength dental polymeric material from said wax-like polymerizable dental material.

5. The method of claim 4 wherein said high strength dental polymeric material is at least a portion of a denture.

6. The method of claim 5 wherein said denture is formed without shaping wax.

7. The method of claim 4 wherein said wax-like polymerizable dental material is shaped into at least a portion of a denture base and polymerized to form polymeric material having an un-notched impact strength of at least 2 foot-pound/inch.

8. The method of claim 4 wherein said polymeric material has an un-notched impact strength of at least 5 foot-pound/inch.

9. The method of claim 8 wherein said polymerizable material is flowable at and above 40° C., dimensionally stable at and below 25° C., and adapted to form polymeric material having a flexural modulus of at least 300,000 psi, and flexural strength of at least 7,000 psi.

10. The method of claim 4 further comprising:
providing shaping said wax-like polymerizable dental material into a form of at least a portion of a dental device, and
curing said wax-like polymerizable dental material to form high strength dental polymeric material having said shape.

11. The method of claim 10 wherein said polymerizable material is heated between 40° C. and 180° C.

12. The method of claim 10 wherein said polymerizable material is flowable at and above 40° C. and further comprising positioning at least one artificial tooth in said polymerizable material.

13. The method of claim 10 further comprising providing an artificial tooth and positioning polymerizable material over said artificial tooth.

14. The method of claim 10 wherein said polymerizable material is adapted to become dimensionally stable within 90 minutes.

15. The method of claim 14 further comprising providing additional polymerizable material, a major portion of said additional polymerizable material being dimensionally stable and a minor portion of said additional polymerizable material being flowable, light curing said additional polymerizable material to form a repaired dental device.

16. The method of claim 10 wherein said polymerizable material is adapted to become dimensionally stable within 5 minutes.

17. The method of claim 10 wherein said dental device is a full denture, partial denture, denture liner, custom tray, artificial tooth, veneer, night guard, splint, retainer, orthodontic component, crown, bridge, dental device, restorative fillings, inlay or onlay.

18. The method of claim 10 further comprising supporting a U-shaped preformed set of artificial teeth on said polymerizable material.

19. A process for making a denture, comprising positioning artificial teeth in wax-like polymerizable dental material.

20. The process of claim 19 wherein said wax-like polymerizable dental material is supported by a base plate, and further comprising shaping said wax-like polymerizable dental material.

21. A method for making a dental product comprising mounting artificial teeth in wax-like polymerizable dental material.

22. The method of claim 21 wherein said wax-like polymerizable dental material is supported by a composition which is not wax-like.

23. The method of claim 21 further comprising polymerizing said wax-like polymerizable dental material to form a portion of said dental product.

24. The method of claim 21 further comprising melting and resolidifing said wax-like polymerizable dental material.

25. A denture comprising: at least one artificial tooth and high strength dental polymeric material formed from wax-like polymerizable dental material.

26. The denture of claim 25 wherein said wax-like polymerizable dental material is shaped into at least a portion of a denture base and polymerized to form high strength dental polymeric material having an un-notched impact strength of at least 2 foot-pound/inch.

27. The denture of claim 26 wherein said wax-like polymerizable dental material is shaped into at least a portion of a denture base and polymerized to form high strength dental polymeric material.

28. A dental product comprising wax-like polymerizable dental material, said wax-like polymerizable dental material being adapted to form high strength dental polymeric material.

29. The dental product of claim 28 wherein said dental product is a full denture, partial denture, denture liner, custom tray, artificial teeth, veneer, denture reline, night guard, splint, retainer, crown, bridge, provisional dental device, inlay, onlay, tooth restorative filling, orthodontic appliance, oral orthopedic appliance, temporary denture, temporary partial denture; maxillofacial prostheses, obturator, or occular prosthesis.

30. The dental product of claim 28 wherein said dental product is a full denture, partial denture, denture liner, custom tray, artificial teeth, denture reline, night guard, splint, retainer, crown, bridge, inlay or onlay.

31. The dental product of claim 28 wherein said dental product is an artificial tooth.

32. The dental product of claim 28 wherein said dental product is a full denture or a partial denture.

* * * * *